(12) United States Patent
Weldon

(10) Patent No.: US 6,560,975 B1
(45) Date of Patent: May 13, 2003

(54) METHOD AND MEANS FOR PAIN-FREE DENTAL INJECTIONS

(76) Inventor: Leonard Weldon, 165 S. Lincoln St., Keene, NH (US) 03431

( * ) Notice: Subject to any disclaimer, the term of this patent is extended or adjusted under 35 U.S.C. 154(b) by 0 days.

(21) Appl. No.: 09/717,188

(22) Filed: Nov. 21, 2000

Related U.S. Application Data
(60) Provisional application No. 60/166,883, filed on Nov. 22, 1999.

(51) Int. Cl.[7] ............................................. A61M 5/00
(52) U.S. Cl. ........................................... 62/117; 62/112
(58) Field of Search ................................. 604/117, 112

(56) References Cited

U.S. PATENT DOCUMENTS

| | | | | |
|---|---|---|---|---|
| 268,996 A | * | 12/1882 | Brinkerhoff | 604/198 |
| 3,508,545 A | * | 4/1970 | Reif et al. | 604/158 |
| 3,662,457 A | * | 5/1972 | Gores | 29/508 |
| 3,995,629 A | * | 12/1976 | Patel | 604/117 |
| 4,275,728 A | * | 6/1981 | Merry | 604/165.04 |
| 4,425,120 A | | 1/1984 | Sampson et al. | 604/198 |
| 4,710,171 A | | 12/1987 | Rosenberg | 604/117 |
| 4,763,667 A | * | 8/1988 | Manzo | 600/563 |
| 4,944,677 A | * | 7/1990 | Alexandre | 433/165 |
| 5,015,235 A | | 5/1991 | Crossman | 604/117 |
| 5,098,389 A | | 3/1992 | Cappucci | 604/158 |
| 5,217,438 A | | 6/1993 | Davis et al. | 604/198 |
| 5,236,419 A | | 8/1993 | Seney | 604/112 |
| 5,240,710 A | * | 8/1993 | Bar-Shalom et al. | 424/401 |
| 5,807,402 A | | 9/1998 | Yoon | 606/185 |
| 5,944,700 A | | 8/1999 | Nguyen et al. | 604/263 |
| 6,139,529 A | * | 10/2000 | Junior | 604/131 |
| 6,287,114 B1 | * | 9/2001 | Meller et al. | 433/80 |

* cited by examiner

*Primary Examiner*—Henry Bennett
*Assistant Examiner*—Filip Zec
(74) *Attorney, Agent, or Firm*—Lynne M. Blank

(57) ABSTRACT

The present invention relates to a dental method and means to allow pain-free injections in mucosa by the application of a topical anesthetic followed by an injection limited to penetrate the mucosa only to the extent of penetration of the topical anesthetic. The method is accomplished by applying a topical anesthetic to the desired mucosal area, and following the topical application with an injection, which penetrates the tissues only to the extent of penetration of the topical anesthetic. Various devices of fixed length are described which limit the penetration of the injection such as a drastically truncated syringe needle, a sheath fitted to and covering the needle, a needle shield, and a speculum.

8 Claims, 6 Drawing Sheets

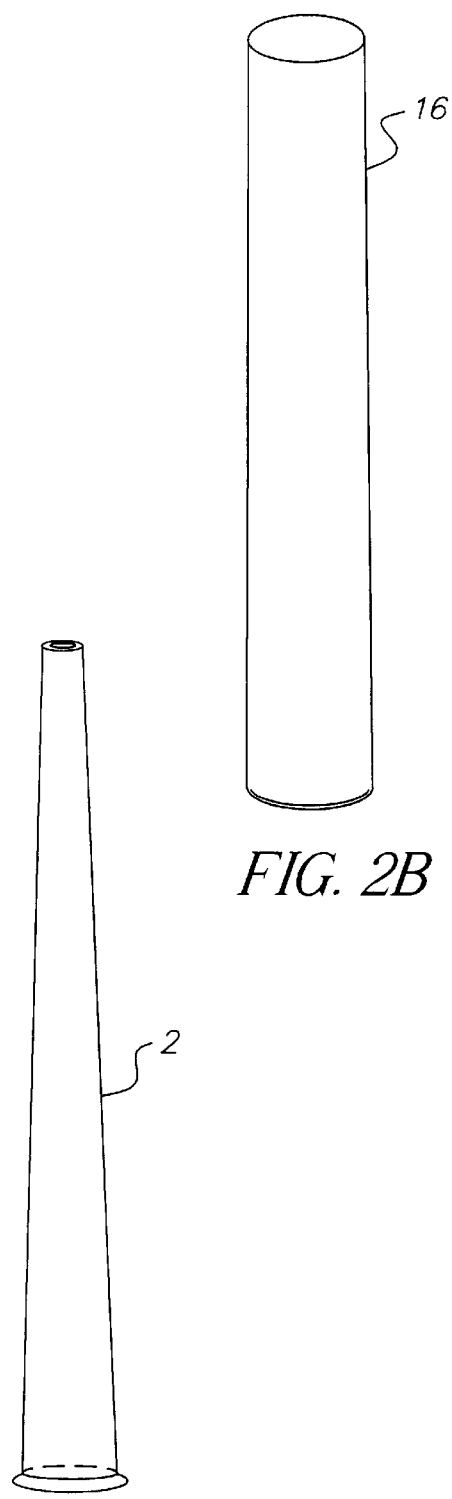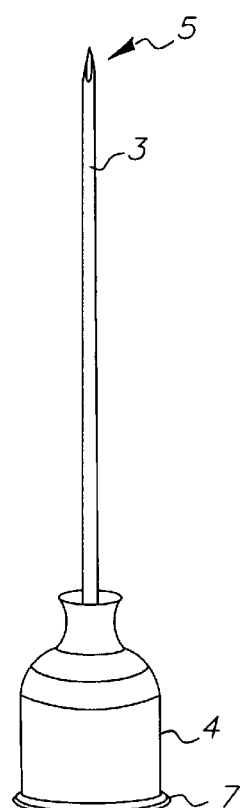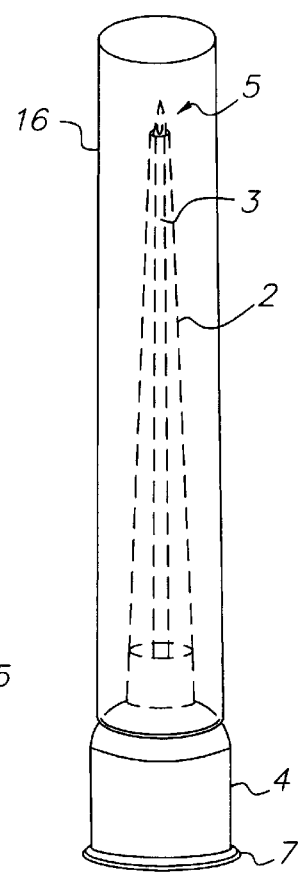
FIG. 2B
FIG. 2C
FIG. 2A
FIG. 2D

METHOD AND MEANS FOR PAIN-FREE DENTAL INJECTIONS

RELATED APPLICATIONS

This application claims benefit of U.S. Provisional Application Ser. No. 60/166,883 filed Nov. 22, 1999, fully incorporated herein by reference.

BACKGROUND OF THE INVENTION

The present invention relates to a dental method and means to allow pain-free injections in mucosa by the application of a topical anesthetic followed by an injection limited to penetrate the mucosa only to the extent of penetration of the topical anesthetic.

It is estimated that 50% of dental patients avoid treatment because of the expected pain, especially pain produced by needles and injections. In addition, stress, in the form of pain, reduces a patient's immunological response. As a result, post-operative recovery times can be extended and the risk of complications increased.

Conventional methods for administering anesthetics to mucosa during dental or oral surgeries employ the application of a topical anesthetic to the mucosa prior to insertion of a hypodermic syringe for delivery of further medications. The depth of penetration of the topical anesthetic ranges typically from 2–4 mm +/–1 mm. The depth of penetration of the hypodermic, typically in excess of 4 mm, exceeds this limited depth of penetration of the topical anesthetic. As a result, although the topical anesthetic reduces the amount of pain experienced prior to the hypodermic injection, the procedure is still painful due to the deeper, unlimited penetration of the hypodermic syringe.

Unlike these other systems, the present invention provides a method that controls the depth of penetration of the hypodermic syringe to less than 4 mm. The syringe is limited in depth of penetration to the depth of mucosa anesthetized by the application of the topical anesthetic. As a result, the patient experiences greatly reduced pain. This in turn leads to shortened recovery time, reduced complications and increases the likelihood that patients in need of treatment will actually seek treatment.

Furthermore, conventional methods for limiting the depth of penetration of needles are designed for use with standard medical needles. Standard medical needles differ considerably from dental needles. Most medical needles are large in size, for use in biopsies, catheterizations, establishment of intravenous tubes, and the like, and have a large bore size in the range of 15 to 18 gauge. Dental needles on the other hand are small, having to fit into a patient's mouth and are of more fragile construction as illustrated by a bore of 27 to 30 gauge. Also, medical needles are typically adjusted to fit the patient and the variable depth, of penetration and have a length greater than 4 mm. Dental needles for anesthetic injections are constant in length, since the depth of penetration required is the same for all patients. Medical needles are typically constructed with a straight shaft, while dental needles include a ring on the shaft to facilitate precise handling during surgery. Medical needles are also constructed for multi-dose vials and the like, while dental needles are specially constructed for set 1.8 mm cartridges. In addition, medical needles are frequently disposable, since the cost of medical procedures allows one-time use. Dental needles, on the other hand, must be re-usable, due to the lower cost requirements and reduced profit margins related to dental procedures. As a result of these marked differences in construction and use requirements between medical and dental needles, the conventional methods for controlling depth of penetration in medical applications are inapplicable to dental anesthetic applications, since the methods are too cumbersome and expensive to be feasible.

The present invention is simple, small and inexpensive, allowing application in dental procedures.

SUMMARY OF THE INVENTION

The present invention is a method and means for accomplishing pain-free injection in mucosa, specifically in dental applications. The method is accomplished by applying a topical anesthetic to the desired mucosal area, and following the topical application with an injection, which penetrates the tissues only to the extent of penetration of the topical anesthetic. Various devices of fixed length are described which limit the penetration of the injection such as a drastically truncated syringe needle, a sheath fitted to and covering the needle, a needle shield, and a speculum.

DESCRIPTION OF THE DRAWINGS

FIG. 2A illustrates the cannula/hub combination of a standard dental syringe.

FIG. 2C more clearly illustrates the appearance of the sheath alone.

FIG. 2D is a perspective view of an alternative means for controlling the depth of the injection to the extent of penetration of the topical anesthetic by means of a sheath fitted completely over the syringe needle equal to the length of the needle minus the extent of penetration of the topical anesthetic, including a syringe cap as shown alone in FIG. 2B.

DESCRIPTION OF THE PREFERRED EMBODIMENT

The preferred method of pain-free injection involves the use of a special topical applicator, one end of which comprises an absorbent means for holding a topical anesthetic and an abrasive area for enhancing the depth of penetration of the topical anesthetic to apply a topical anesthetic to dental mucosa. Further medications are then delivered into the area of mucosa anesthetized by the topical by means of a device controlling the depth of penetration of a hypodermic syringe.

Figure 1:
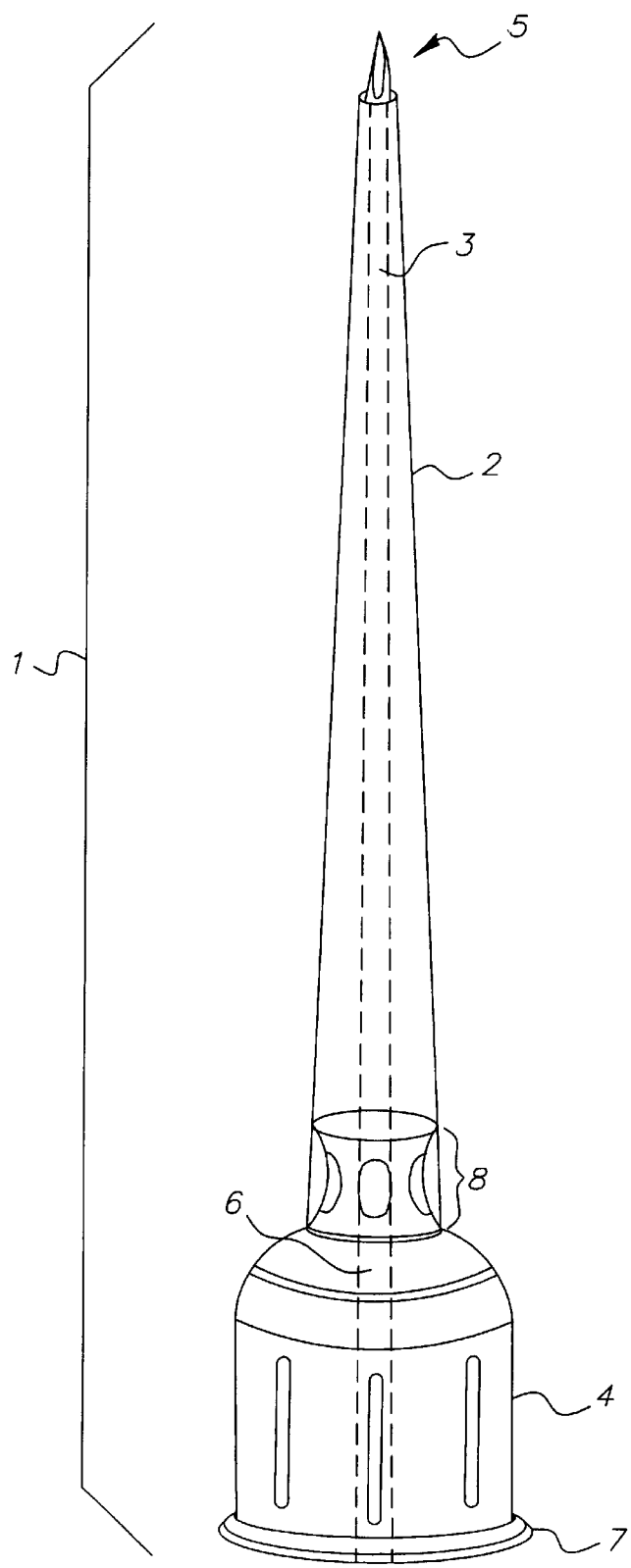
FIG. 1 is a perspective view of the preferred embodiment for controlling the depth of the injection to the extent of penetration of the topical anesthetic by means of a sheath fitted completely over the syringe needle equal to the length of the needle minus the extent of penetration of the topical anesthetic.

The preferred means for controlling the depth of penetration of the hypodermic syringe is illustrated by FIG. 1. The preferred means comprises a cannula/hub assembly 1 surrounded completely by a sheath 2. The cannula/hub assembly 1 includes a hollow cannula 3, attached to a front end 8 of hub 4 at one end with the opposite bevel end 5 open and sharpened for insertion into the mucosa. The hub 4 includes a passage 6 extending therethrough, which is preferably transparent to allow the user to detect the presence of fluid therein. The rear end of the hub 7 is formed to facilitate the attachment of a syringe body thereto.

The sheath 2 surrounds cannula 3, contacting the front end 8 of the hub 4 and extending completely over the length of cannula 3 to a distance from open end 5 of cannula 3 equal to but not greater than the depth of penetration of the topical anesthetic into the mucosa.

Sheath 2 may be made of any material commonly used in medical devices such as stainless steel, rubber, elastomer or plastic. Sheath 2 is long enough to cover the length of the cannula from the hub to a distance from the opposite bevel end such that less than 4 mm of the opposite bevel end of the cannula is exposed.

FIG. 2D is a perspective view of the sheath device illustrated in FIG. 1, including a syringe cap 16.

Figure 3:
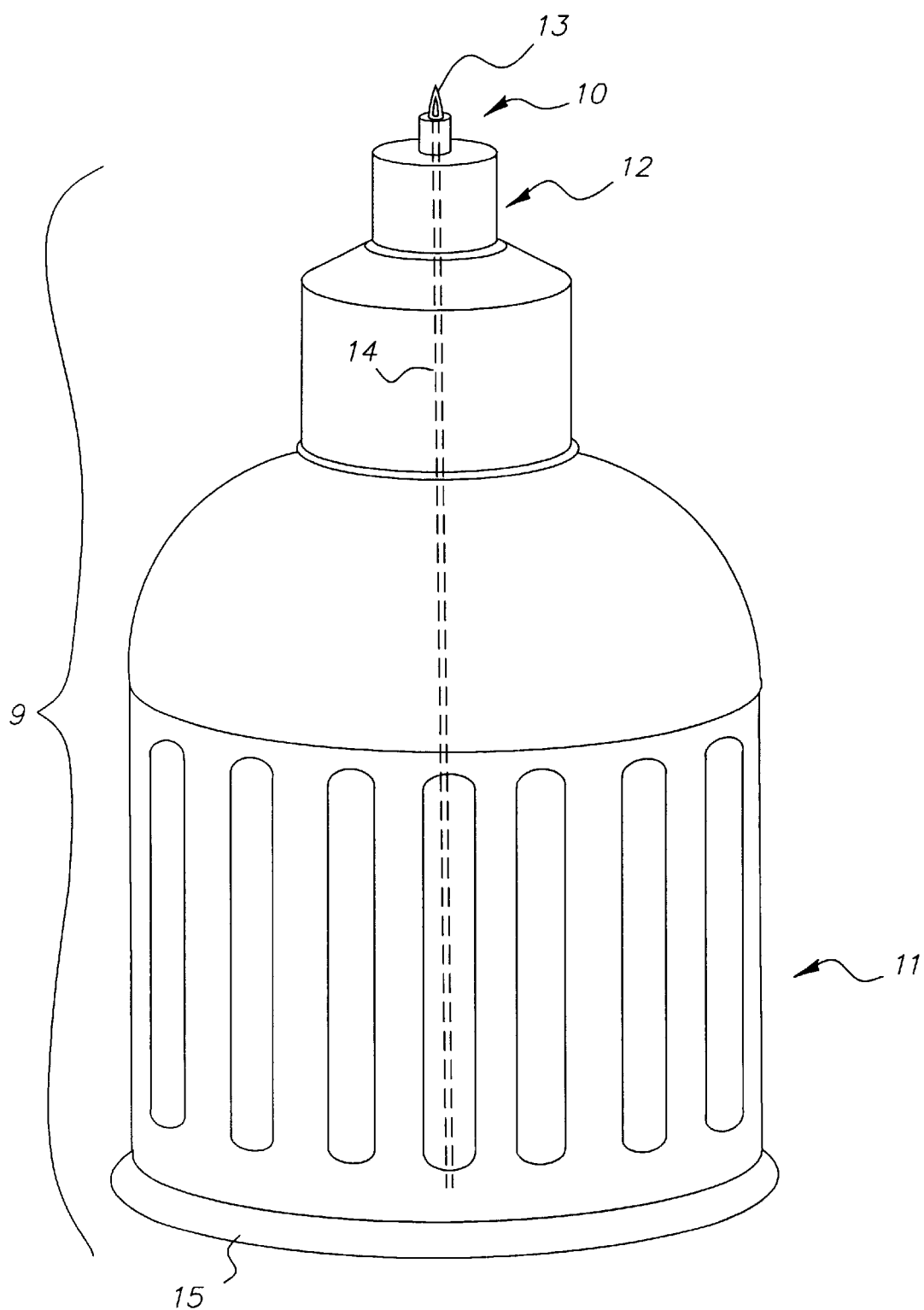
FIG. 3 is a perspective view of a means for controlling the depth of the injection to the extent of penetration of the topical anesthetic by means of a syringe having a needle of fixed length.

FIG. 3 is a perspective view of an alternative means for controlling the depth of the injection. This alternative employs a cannula/hub assembly 9. The cannula/hub assembly 9 includes a hollow, very short cannula 10, no longer than the depth of penetration of the topical anesthetic, attached to a front end/needle base 12 of hub 11 at one end with the opposite bevel end 13 open and sharpened for insertion into the mucosa. The hub 11 includes a passage 14 extending therethrough, which is preferably transparent to allow the user to detect the presence of fluid therein.

The rear end of the hub 15 is formed to facilitate the attachment of a syringe body thereto. The length of short cannula 10 will typically be less than 4 mm.

Figure 4:
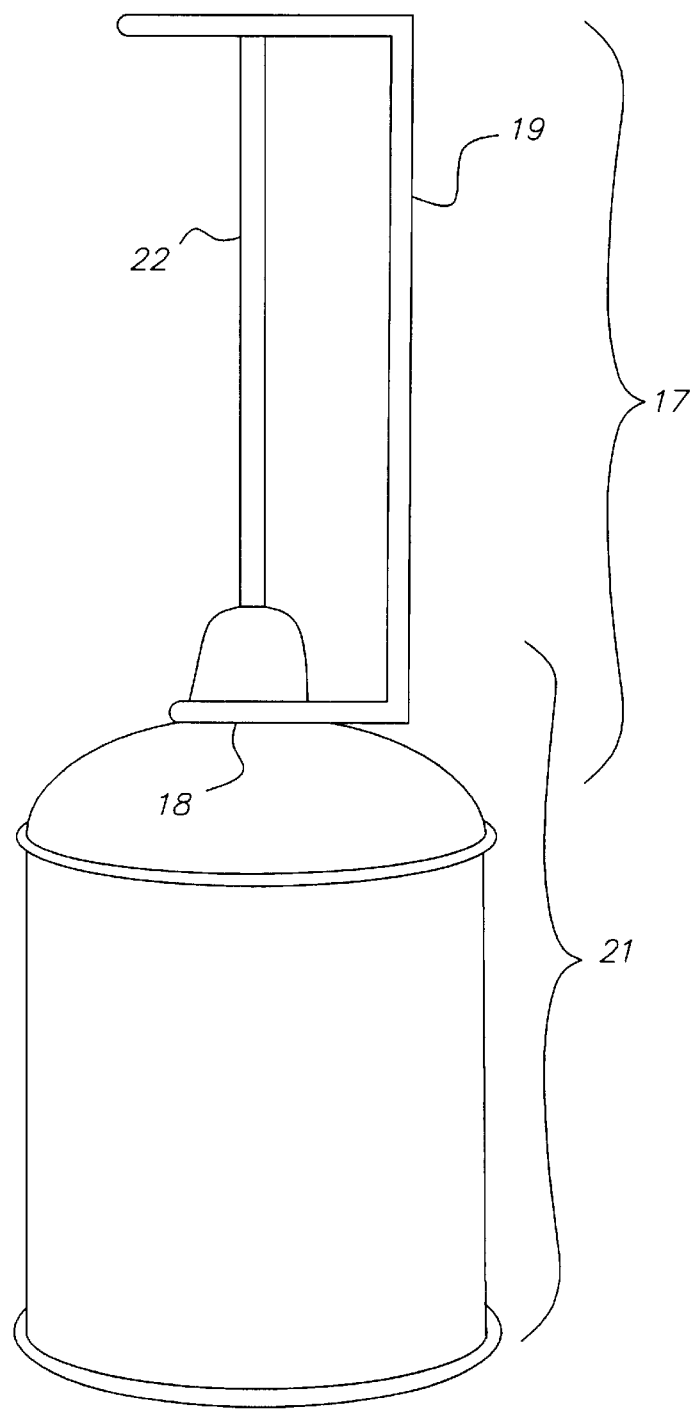
FIGS. 4 and 5 are perspective views of an alternative means for controlling the depth of the injection to the extent of penetration of the topical anesthetic by means of a needle shield or snap guard partially covering the needle and equal to the length of the needle minus the extent of penetration of the topical anesthetic.
Figure 5A:
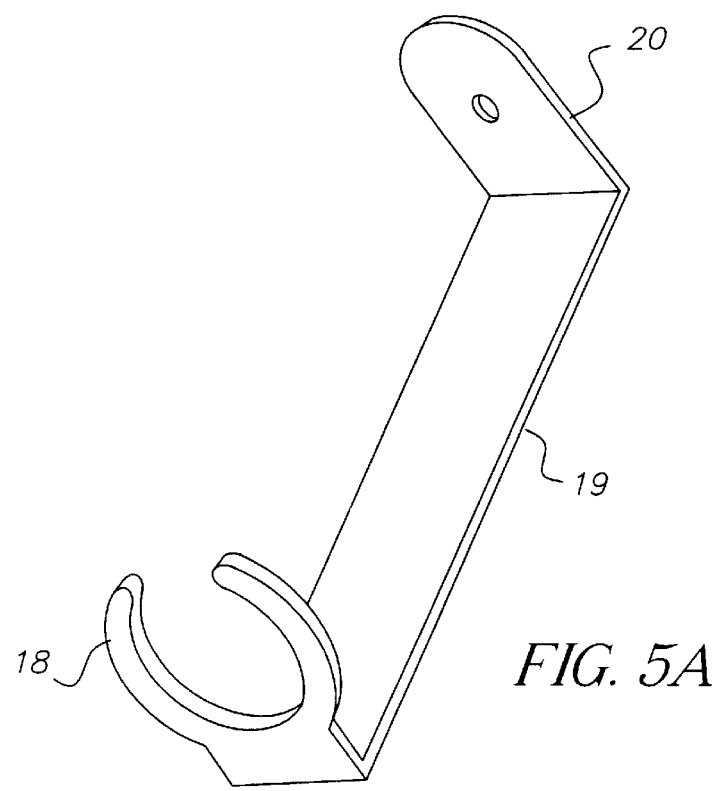
Figure 5B:
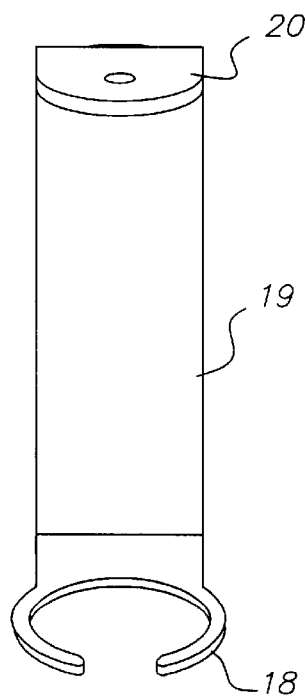
Figure 5C:
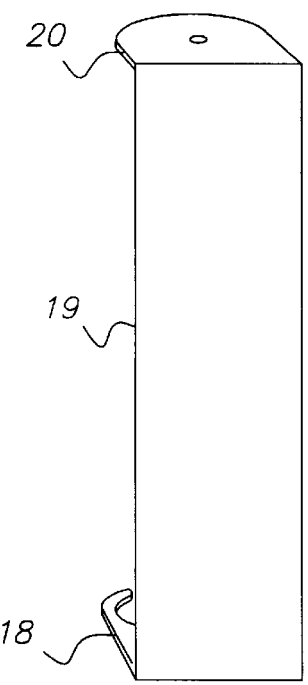

FIGS. 4 and 5 illustrate an additional means of controlling depth of penetration of the hypodermic syringe. This method involves a needle shield or snap guard partially covering the needle and equal to the length of the needle minus the extent of penetration of the topical anesthetic. The shield 17 comprises a hub collar 18, a guard shaft 19 and a needle shield 20. The hub collar removably attaches to hub 21 at the end of hub 21, which attaches to needle 22. The hub collar attaches at an angle to the guard shaft 19, which has a length sufficient to stretch the length of needle 22 minus the depth of penetration of the topical anesthetic into the mucosa. This length exposes approximately 4 mm or less of the cannula. The needle shield 20 attaches at an angle to the guard shaft and has an opening to allow passage of cannula 22.

To use these devices, the dentist first applies a topical anesthetic to the desired mucosal area by any standard application means known to those skilled in the art. The application is followed by an injection given by the above-described devices. The depth of the injection is automatically limited by these devices to penetrate only into the area anesthetized by the topical. As a result, the patient experiences greatly reduced discomfort and pain.

Figure 6B:
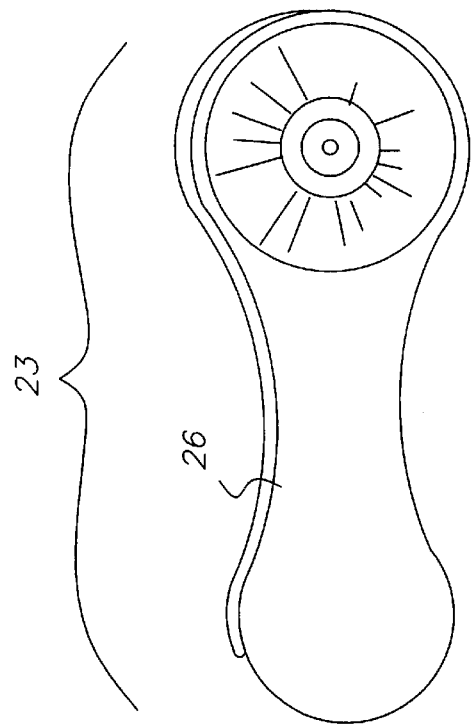
FIG. 6 is a perspective view of an alternative means for controlling the depth of the injection to the extent of penetration of the topical anesthetic by means of a covering speculum equal to the length of the needle minus the extent of penetration of the topical anesthetic.
Figure 6A:
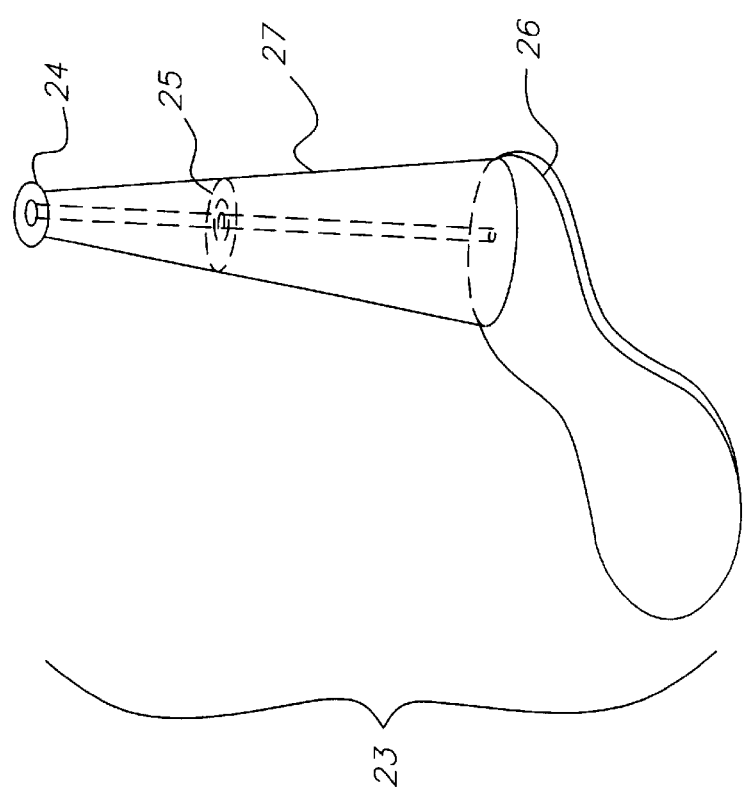

FIG. 6 is a perspective view of an yet another alternative means for controlling the depth of the injection to the extent of penetration of the topical anesthetic by means of a covering speculum equal to the length of the needle minus the extent of penetration of the topical anesthetic. The speculum 23 comprises a handle 26 attached at one end at an angle to a hollow speculum shaft 27. Speculum shaft 27, in turn, attaches at one end to speculum handle 26. The other end of the speculum shaft comprises an opening or needle port 24 to allow passage of the hypodermic syringe cannula. Located inside the speculum shaft 27 and attached thereto is needle stop 25. Needle stop 25 is located so as to limit the extension of the hypodermic syringe through the needle port 24 to the depth of penetration of the topical anesthetic into the mucosa, again, approximately 4 mm or less.

In order to use this device, the dentist applies a topical anesthetic to the desired mucosal area by any standard application means known to those skilled in the art. The dentist then places the speculum 23 in the patient's mouth with the needle port 24 in the area of the topical application. The dentist then inserts the hypodermic syringe into the speculum 23 and makes the injection. The needle stop 25 in the speculum 23 automatically limits the depth of penetration to, that region anesthetized by the application of the topical anesthetic.

While I have illustrated and described several embodiments of my invention herein, it will be understood that these are by way of illustration only and that various changes and modifications may be contemplated in my invention and within the scope of the following claims.

What is claimed is:

1. A method for pain-free injections in mucosal tissues comprising:
    applying topical anesthetic to an area of mucosal tissues;
    allowing penetration into said area by said topical anesthetic; and
    injecting into said area no deeper than said penetration by said topical anesthetic.

2. A method for pain-free injections in mucosal tissues comprising:
    abrading an area of mucosal tissue;
    applying a topical anesthetic to said area;
    allowing penetration into said area by said topical anesthetic; and
    injecting into said area no deeper than said penetration by said topical anesthetic.

3. A device for controlling the depth of penetration of a needle comprising:
    a cannula/hub assembly, comprising:
        a hub, having:
            a front end;
            a rear end, said rear end formed to facilitate the attachment of a syringe body thereto; and
            a passage extending therethrough said hub between said front end and said rear end;
        a hollow cannula, having:
            an end attached to said front end of said hub; and
            an opposite bevel end, said opposite bevel end of which is open and sharpened for insertion into the mucosa;
        a sheath, said sheath having:
            a proximal end, said proximal end being removably attached to said front end of said hub;
            a distal end, said distal end being located a distance from said opposite bevel end of said cannula; and
            a length, said length extending to said distance from said opposite bevel end of said cannula, said distance being equal to but not greater than the depth of penetration of the topical anesthetic into the mucosa.

4. A device as described in claim 3, further comprising:
    a hollow syringe cap, having:
        a proximal end, said proximal end being removably attached to said front end of said hub, and covering said sheath;

a distal end, said distal end being located a distance beyond said opposite bevel end of said cannula; and a length, said length extending beyond said opposite bevel end of said cannula, said length being greater than the length of said cannula.

5. A device for controlling the depth of penetration of a needle comprising:

a cannula/hub assembly, comprising:
  a hub, having:
    a front end;
    a rear end, said rear end formed to facilitate the attachment of a syringe body thereto; and
    a passage extending therethrough said hub between said front end and said rear end;
  a hollow cannula, having:
    an end attached to said front end of said hub;
    an opposite bevel end, said opposite bevel end of which is open and sharpened for insertion into the mucosa; and
    a length no greater than the depth of penetration of a topical anesthetic into mucosal tissue.

6. The device of claim 5, wherein said length of said hollow cannula is no greater than 1.5 mm.

7. A device for controlling the depth of penetration of a needle comprising:

a cannula/hub assembly, comprising:
  a hub, having:
    a front end;
    a rear end, said rear end formed to facilitate the attachment of a syringe body thereto; and
    a passage extending therethrough said hub between said front end and said rear end;
  a hollow cannula, having:
    an end attached to said front end of said hub; and
    an opposite bevel end, said opposite bevel end of which is open and sharpened for insertion into the mucosa;
  a guard partially covering said hollow cannula, comprising:
    a hub collar having:
      a collar end removably attached to said front end of said hub; and
      a shaft end;
    a guard shaft, having
      a collar attachment end, said attachment collar end attached to said shaft end of said hub collar;
      a shield attachment end;
      a length, equal to the length of the needle minus the extent of penetration of the topical anesthetic; and
    a needle shield, having
      a guard shaft end, said guard shaft end attached to said shield attachment end of said guard shaft; and
      an opening to allow passage of said cannula.

8. Speculum for controlling the depth of penetration of a needle comprising:

a hollow speculum shaft, having a proximal end, a distal end, and a length;

a handle, said handle attached to said proximal end of said hollow speculum shaft;

a needle port to allow passage of the hypodermic syringe cannula, said needle port comprising an opening in said distal end of said hollow speculum shaft; and a needle stop, located inside said hollow speculum shaft and attached thereto at a distance from said needle port equal to or greater than the length of the needle minus the depth of penetration of the topical anesthetic into the mucosa.

* * * * *